United States Patent
Jakobs-Sauter et al.

(10) Patent No.: US 9,758,715 B2
(45) Date of Patent: Sep. 12, 2017

(54) HIGHLY-CONCENTRATED FLOWABLE SALTS OF ALKYL POLYALKOXY SULPHATES

(75) Inventors: Britta Jakobs-Sauter, Langenfeld (DE); Uwe Kaltwasser, Marl (DE)

(73) Assignee: Sasol Germany GmbH, Hamburg (DE)

( * ) Notice: Subject to any disclaimer, the term of this patent is extended or adjusted under 35 U.S.C. 154(b) by 95 days.

(21) Appl. No.: 14/006,993

(22) PCT Filed: Mar. 23, 2012

(86) PCT No.: PCT/EP2012/001275
§ 371 (c)(1),
(2), (4) Date: Dec. 3, 2013

(87) PCT Pub. No.: WO2012/126630
PCT Pub. Date: Sep. 27, 2012

(65) Prior Publication Data
US 2014/0083707 A1    Mar. 27, 2014

(30) Foreign Application Priority Data
Mar. 24, 2011   (DE) .................. 10 2011 015 046

(51) Int. Cl.
| | | |
|---|---|---|
| C09K 8/06 | (2006.01) | |
| C09K 8/584 | (2006.01) | |
| C07C 303/24 | (2006.01) | |
| C07C 303/42 | (2006.01) | |
| C11D 1/29 | (2006.01) | |
| C10M 135/10 | (2006.01) | |
| C10M 151/04 | (2006.01) | |
| E21B 43/16 | (2006.01) | |

(52) U.S. Cl.
CPC ............ *C09K 8/584* (2013.01); *C07C 303/24* (2013.01); *C07C 303/42* (2013.01); *C10M 135/10* (2013.01); *C10M 151/04* (2013.01); *C11D 1/29* (2013.01); *E21B 43/16* (2013.01); *C10M 2219/044* (2013.01); *C10M 2221/04* (2013.01); *C10N 2240/40* (2013.01); *C10N 2270/02* (2013.01)

(58) Field of Classification Search
CPC .............................. C09K 8/584; C09K 8/602
USPC ................................... 507/136, 254
See application file for complete search history.

(56) References Cited

U.S. PATENT DOCUMENTS

| | | |
|---|---|---|
| 3,843,706 A | 10/1974 | Weil et al. |
| 4,303,556 A * | 12/1981 | Llendado .............. 510/452 |
| 4,483,787 A * | 11/1984 | Jones et al. ............ 510/424 |
| 4,592,875 A | 6/1986 | Kesling, Jr. et al. |
| 4,608,197 A * | 8/1986 | Kesling et al. ........... 510/537 |

FOREIGN PATENT DOCUMENTS

EP    0167337    6/1985

OTHER PUBLICATIONS

Scheibel, Production of Alcohols and Alcohol Surfactants, Handbook of Detergents, 2009, p. 118.
Wu, et al., Branched Alkyl Alcohol Propoxylated Sulfate Surfactants for Improved Oil Recovery, Tenside Surf. Det., vol. 47, 2010, p. 152-161.

* cited by examiner

Primary Examiner — Aiqun Li
(74) Attorney, Agent, or Firm — Bushman Werner, P.C.

(57) ABSTRACT

The present invention is directed to highly-concentrated compositions of salts of alkyl polyalkoxy sulphates, whereby in total at least ⅔ of all alkoxy unit of the alkyl polyalkoxy sulphates are propoxy units.

38 Claims, No Drawings

HIGHLY-CONCENTRATED FLOWABLE SALTS OF ALKYL POLYALKOXY SULPHATES

CROSS REFERENCE TO RELATED APPLICATION

This application is U.S. National of international application PCT/EP2012/001275, filed on Mar. 23, 2012, which claims priority to DE 102011015046 filed on Mar. 24, 2011, the disclosures of which are incorporated herein by reference for all purposes.

FIELD OF THE INVENTION

The present invention relates to highly-concentrated compositions of salts of alkyl polyalkoxy sulphates, wherein in total at least ⅔ of all alkoxy units of the salts of alkyl polyalkoxy sulphates are proproxy units, a method of producing the composition and their use in oil and gas field applications.

BACKGROUND OF THE INVENTION

Alkyl polyalkoxy sulphates often also called alkyl polyether sulphates, (fatty) alcohol polyglycol ether sulphates or (fatty) alcohol polyether sulphates, commonly known and referenced hereunder in short as ether sulphates or alkyl ether sulphate salts, are used as surfactants or emulsifiers in numerous consumer products such as cleaning agents, shampoos and cosmetics. Structurally they have a lipophilic alkyl group and a hydrophilic area composed of the polar ether groups and the chemically bonded sulphate anion. These physical properties make these compounds surfactants and allow them to emulsify fats and oils. They are not very sensitive to hard water and are generally easily biodegradable. Fatty alcohols are understood hereunder to reference C8- to C18-branched and/or unbranched aliphatic mono-alkanols.

Alkyl ether sulphates can be produced from fatty alcohols in that fatty alcohols are initially converted with alkylene oxide, usually ethylene oxide. EO references ethylene oxide or an ethylene oxide group (—CH$_2$CH$_2$O—). The average number of ether groups is normally between 1 and 12. The hydroxyether is then converted to an ester with sulphur trioxide which results in a sulphuric acid monoester or a sulphuric acid semiester. This acid is unstable and is converted into a salt with the use of alkali hydroxide or ammonia. Common commercial forms in the case of sodium ether sulphates with 2 or 3 EOs are aqueous paste-like compositions with a concentration of approximately 70% by weight or aqueous liquid compositions comprising up to 28% by weight anionic active substances (in each case measured as anionic active substance in accordance with DIN ISO 2271). Concentration ranges between approximately 30% by weight and below approximately 70% by weight active content (anionic active substance) result in non-flowable and non-pumpable compositions, as liquid crystalline structures in the form of hexagonal or cubic phases with a very high viscosity are formed. These often constitute a problem when diluting 70% ether sulphate pastes, which have a lamellar liquid crystalline structure, to the desired usage concentration.

Concentrations of slightly over 70% by weight and more are also no longer flowable or pumpable as crystallisation of the ether sulphate begins, whereas concentrations of around 70% by weight are often found to be flowable and pumpable.

Several solutions to prevent very high viscosities in ether sulphates have been described in the literature, such as the use of alkyl- or alkanol-amines as neutralizing agents or addition of organic solvents like alkylene glycols or short chain alcohols or polyalkylene sulphates or nonionic surfactants such as alcohol alkoxylates as viscosity reducers. Viscosity reducers need to be present in significant amounts, meaning more than the usual residual unsulphated matter under standard sulphation conditions. This can be achieved by either intentional incomplete sulphation reaction or by adding viscosity reducers in the neutralization step.

Whereas the use of alcohol ether sulphates containing ethylene-oxy/ethylenoxide units as ether groups is well known in personal care, washing and cleaning formulations as well as in industrial applications, for example as emulsifiers for emulsion polymerisation, ether sulphates containing propylene-oxy units are less familiar on the market. To date, only up to 40% solutions of alkali fatty alcohol (poly)propoxy sulphates are available in a convenient, i.e. flowable and pumpable, viscosity range, and no supply forms which dissolve both in water and in oils are known.

For use in industrial applications such as textile and leather auxiliary agents, metal working and lubricants, oil and gas field chemicals or tertiary oil recovery, surfactants or emulsifiers are required which exhibit a high emulsifying effect for various oils with water. Products with a high active content are required in order to keep the amount used and raw material and transport costs associated therewith as low as possible. The products should also be available in the form of flowable and pumpable material which is as homogenous as possible, as this is the simplest form of transporting, storing and dispensing them for use. The products should be essentially free of organic solvents and/or other viscosity reducers, have a low salt content, mix well with water and oils and be easily dilutable to the desired usage concentration. In addition, as low a pour point as possible is desirable which allows it to be used at low temperatures.

SUMMARY OF THE INVENTION

The aim of the present invention is to find a highly-concentrated form of salts of alkylpolyalkoxysulphates, which is flowable at least at room temperature (25° C.), more particularly in the range from 10° C. to 35° C., and is essentially free of organic solvents or other viscosity modifying additives, dissolves easily in both water and oils, can be easily diluted and has a pour point considerably below −5° C. and more particularly even below −15° C.

This objective was achieved by the subject of the independent claims. Surprisingly it was found that highly-concentrated alkylpolyalkoxysulphate compositions containing
a) more than 75% by weight, preferably more than 80% by weight salts of alkyl polyalkoxy sulphates,
  wherein the alkyl polyalkoxy sulphates have in average 3 to 20 alkoxy groups, at least ⅔ of all alkoxy groups of the alkyl polyalkoxy sulphates are propoxy groups and the alkyl residue is a fatty alcohol residue with 8 to 18 carbon atoms and
b) 1 to below 25% by weight water, preferably 1 to below 20% by weight water, satisfy the above requirements.

Particularly preferred as salts of alkyl polyalkoxy sulphates are those in which—if present—the various alkoxy units are present in one molecule chain (and not only as a mixture of homoalkoxylates) and more particularly alkyl polypropoxy sulphates (also known in simplified form as (fatty) alcohol proproxy sulphates).

In contrast, fatty alcohol ethoxy sulphate pastes or fatty alcohol propoxy sulphates with smaller active contents are no longer flowable or pumpable or not easy to dilute or have higher pour points or are insoluble in oil or exhibit a combination thereof.

DETAILED DESCRIPTION OF PREFERRED EMBODIMENTS

Preferred forms of embodiment form the subject matter of the sub-claims or are described below.

Suitable for use as fatty alcohols or fatty alcohol residues are linear or branched primary alcohols with 8 to 18 carbon atoms, preferably with 12 to 17, more particularly with 12 to 15 carbon atoms, and preferably more particularly mixtures containing at least more than 25 mol % branched primary alcohols.

Particularly suitable are the above fatty alcohols or alcohol residues with more than 40 mol % branched portions and very particularly fatty alcohols with on average at least one branch per molecule, more particularly (greater than 50%) on the C2, C3 or C4 carbon atom, more particularly on the C2 carbon atom. The branching preferably has 1, 2, 3 and/or 4 carbon atoms.

The alkoxylation takes place with an average of 3 to 20 alkoxy groups, preferably 3 to 16 in accordance with the methods known to a person skilled in the art, whereby the alkoxylates can exhibit a conventional or a narrow homolog distribution. Contents of ethylene oxide groups or higher alkylene oxide such as butylene oxide groups are possible, if at least ⅔ of all alkoxy groups are propylene oxide. Particularly preferably the alkoxylate exclusively has 3 to 13, more particularly 4 to 10, propoxy groups.

The sulphation of the alcohol propoxylates can take place a in known manner for fatty alcohol ether sulphates with the usual methods, whereby the use of falling film reactors is preferred. As sulphation agents oleum, chlorosulphonic acid, amidosulphonic acid (sulfamic acid) or more particularly sulphur trioxide, for example, can be considered, whereby the latter is used diluted with an inert gas. The resulting sulphuric acid semi-ester is not stable and must therefore immediately be transferred into a neutralisation cycle in which it is converted, under high shear, with as highly concentrated aqueous alkali hydroxide as possible, more particularly 50% sodium hydroxide solution. In the preferred forms of embodiment the temperature during neutralisation is kept at 45 to 65° C., more particularly 50 to 60° C., at a pH value (related to 1% of the product in water) of pH 10 and higher, more particularly at least 11 and higher, in order to avoid viscosity peaks in the medium concentration ranges.

The thus obtained highly-concentrated alcohol ether sulphate (salt) contains smaller portions of alcohols, propylene glycols (also sulphated) and alcohol propoxylates. The proportion of unsulphated material in the end product is typically 0 to 10% by weight, preferably 0 to less than 5% by weight. The content of alkyl polyalkoxy sulphate salts in accordance with the invention in the compositions is more than 75% by weight, more particularly more than 80% by weight, preferably more than 82% by weight and more particularly up to 95% by weight.

The obtained product can, but does not have to be mixed with commercially available preservatives and/or buffers in order to increase the stability to chemical decomposition and/or the stability to microorganisms in possibly diluted form. In a preferred form of embodiment 0.05 to 5% by weight, more particularly 0.1 to 2% by weight of citric acid is added to the product.

The compounds are used as an oil-soluble lubricant, e.g. in metal working, but more particularly as a surface active substance (surfactant) for deployment in improved or tertiary crude oil recovery. Together with the entrapped crude oil, the aqueous surfactant solution, which can also contain other components such as polymers, solvents, co-surfactants, salts, alkalisation agents, preserving agents, forms a micro-emulsion which is characterised by an extremely low interfacial tension and can thereby solubilise and mobilise the oil.

The flowability of a liquid phase depends on many external factors such as the temperature, the container, the pump and the viscosity. In connection with the invention flowable means that at a temperature of 25° C. and a shear rate of $D=10 \ s^{-1}$ the compound has a viscosity of less than 10000 mPas, preferably even less than 5000 mPas. The viscosity can be determined with the aid of commercially available measuring devices such as rotational viscometers or rheometers with cone/plate measuring geometry in accordance with DIN 53019.

The oil solubility of the compound in accordance with the invention is preferably at least 5% by weight in paraffin oil (e.g. Merkur® WOP 100 PB) or mineral oil (e.g. Shell Gravex® 915), whereby at 25° C. gentle stirring results in a clear solution.

To determine the dilutability, at room temperature (25° C.) the product is mixed with water at such a ratio that a 20% by weight solution (anionic active substance) is produced. If this can take place in a glass beaker through manual stirring with a spatula or glass rod without passing through highly viscous states which can no longer be stirred and therefore mixed by hand the product is by definition easily dilutable. If not, the product cannot be easily diluted in water.

In connection with this invention the pour point means that (in accordance with ASTM D97-09) the product is cooled in 3° C. steps. If after 10 minutes at this temperature it does not flow within 5 seconds of tilting the container into the horizontal, the 3° C. higher value is taken as the pour point.

Example 1

A branched primary C12/C13 alcohol (ISALCHEM® 123) with on average 8 propoxy groups was sulphated in a continuous sulphation apparatus.

Raw material: ISALCHEM® 123+8 PO(OH number: 83.2 mg KOH/g, water: 0.03%, molecular weight: 674.3 g/mol). At a $V_2O_5$ catalyst gaseous $SO_2$ was converted to $SO_3$ at high temperature. The gas was cooled and diluted with air (dew point −60° C.). The proportion of $SO_3$ in the air was 7% by volume.

In a falling film reactor with distributors the propoxylated alcohol was made to react with the $SO_3$/air mixture. The reaction gas flows though the falling film reactor at high speed and generates high turbulences on contact with the propoxylated alcohol. This resulted in an intensive exchange of substances. Intensive cooling of the falling film reactor ensures the removal of the reaction heat. Gas/liquid separation was carried out at the outlet of the falling film reactor. The fluid phase is taken for neutralisation, the gaseous phase for exhaust gas treatment.

The product is pumped around in a neutralisation circuit with the appropriate neutralisation medium. A pH value regulator adds the appropriate quantity of alkaline components, in this case aqueous NaOH, 50% by weight. At the same time the product is homogenised in the circuit though a very highly shearing mixer tool. The finished product was removed continuously from the neutralisation circuit. 0.1% by weight citric acid was added to the finished product.

The conversion parameters were as follows:
Temperature in the converter: 450° C.
$SO_3$ concentration in the reaction gas: 7% by volume
Molar ratio propoxylate/$SO_3$: $SO_3$ in excess
Quantity used (propoxylate): 3.9 kg/hour
hydroxyl number material used: 83.2 mg KOH/g
Temperature at the lower outlet of the falling film reactor: 25-30° C.
Theoretical acid number, sulphuric acid semi-ester: 74.4 mg KOH/g
Actual acid number, sulphuric acid semi-ester 94 mg KOH/g
Temperature neutralisation circuit: 55-60° C.
A product with the following composition was obtained:
Anionic active substance 90+/−1% by weight (DIN ISO 2271)
Unsulphated material (non-ionic substance): <1% by weight % (DIN EN 13273)
$Na_2SO_4$: 0.55% by weight
Free alkali: 0.01% by weight ing alcohol propoxy sulphate salts. The obtained compounds and properties are out in table 1 below.

Comparative Examples (Not in Accordance with the Invention)

ISALCHEM™ 123+8PO $SO_3Na$, anionic active 26.7% by weight, unsulfphated material 2.6% (calculated on 100% by weight active): not clearly soluble in mineral oil and paraffin oil, pour point −6° C.

ISALCHEM™ 145+8PO $SO_3Na$, anionic active 33.3% by weight, unsulphated material 9.4% (calculated on 100% by weight active): not clearly soluble in mineral oil and paraffin oil, pour point +3° C.

MARLINAT™ 242/70 (C12C14+2EO $SO_3Na$, anionic active 70% by weight): not clearly soluble in mineral oil and paraffin oil, not easily dilutable.

SAFOL™ 23 2EO $SO_3Na$, anionic active 70 wt. %: not clearly soluble in mineral oil and paraffin oil, not easily dilutable.

ALFOL™ 1218 7EO (narrow range) $SO_3Na$, high active (>75 wt. % anionic active matter): viscosity at 25° C./10 $s^{-1}$>20000 mPas, not easily dilutable

TABLE 1

|  | ISALCHEM 145 + 8 PO $SO_3Na$ | LIAL 145 + 3.8 PO $SO_3Na$ | LIAL 145 + 9.8 PO $SO_3Na$ | SAFOL 23 + 6.5 PO $SO_3Na$ | SAFOL 23 + 12.5 PO $SO_3Na$ | Linear C12 + 12.8 PO $SO_3Na$ | Linear C12C14 + 4 PO $SO_3Na$ |
|---|---|---|---|---|---|---|---|
| Anionic active substance, a-WAS (% by weight) | 89.2 | 89.3 | 83.0 | 89 | 83 | 89 | 80 |
| Unsulphated material (% by weight) | 2.1 | 2 | 9 | 1 | 3 | 7 | <1 |
| $Na_2SO_4$ (% by weight) | 0.6 | 0.4 | 0.6 | 0.3 | 0.3 | 0.5 | 0.3 |
| Free alkali (% by weight) | 0.04 | 0.04 | 0.7 | 0.1 | 0.1 | 0.1 | 1.6 |
| Water (% by weight) | 8.1 | 10.6 | 8 | 8 | 6 | 6 | 17 |
| pH 1% in water | 9.5 | 9.5 | 11.1 | 10.1 | 9.9 | 9.1 | 11.6 |
| Pour point (° C.) | −21 | −18 | −21 | <−24 | <−24 | <−24 | n.d. |
| 5% t.q. in mineral oil | Clear | Clear | Clear | Clear | Clear | Clear | Clear |
| Viscosity (mPas, at pH >11, 25° C. and 10 $s^{-1}$) | 1300 | 1600 | 1200 | 1000 | 1200 | 1050 | 9000 |
| Easily dilutable | Yes | Yes | Yes | Yes | Yes | Yes | Yes |

Water: around 10% by weight
with the following properties:
pH 1% in water: 9.3
Pour point: −24° C.
5% tel quel in paraffin oil: clearly soluble
5% t.q. in mineral oil: clearly soluble
Viscosity (in mPas, at pH>11.25° C. and 10 $s^{-1}$): 1100

Other Examples

In an analogue manner to example 1 a branched primary C14/C15 alcohol (ISALCHEM® 145) with on average 8 propoxy groups, a partially branched primary C14/C15 alcohol (LIAL® 145) with on average 3.8 PO (propoxy) groups, a partially branched primary C14/C15 alcohol (LIAL® 145) with on average 9.8 PO groups, a partially branched primary C12/C13 alcohol (SAFOL® 23) with on average 6.5 PO groups, a partially branched primary C12/C13 alcohol (SAFOL® 23) with on average 12.5 PO groups, a partially branched primary C16/C17 alcohol (LIAL® 167) with on average 4 PO groups, a linear C12 alcohol with on average 12.8 PO groups and a linear C12/C14 alcohol with on average 4 PO groups were converted to the correspond-

The invention claimed is:
1. Highly-concentrated alkyl polyalkoxy sulphate composition, comprising:
   a) more than 80% by weight salts of alkyl polyalkoxy sulphates, whereby the alkyl polyalkoxy sulphates have in average 3 to 20 alkoxy groups, at least ⅔ of all alkoxy groups of the alkyl polyalkoxy sulphates are propoxy groups and the alkyl residue is a fatty alcohol residue with 13 to 18 carbon atoms or is a mixture of C12 and C13 fatty alcohol residues and
   b) 5 to below 20% by weight water;
   said compositions being flowable at least at 25° C., wherein flowable means having a viscosity of below 10000 mPas measured in accordance with DIN 53019 at 25° C. and with a shear rate of D=10 $s^{-1}$.

2. Composition in accordance with claim 1, whereby the fatty alcohol residue has 13 to 17 carbon atoms.

3. The composition of claim 2, wherein the fatty alcohol residue has 13 to 15 carbon atoms.

4. Composition in accordance with claim 1, wherein the fatty alcohol residue is present in the form of a mixture containing branched fatty alcohol residues.

5. The composition in accordance with claim 4, wherein the fatty alcohol residue contains more than 40 mol % branched fatty alcohol residues.

6. Composition is accordance with claim 4, wherein more than 50% of the branches are on the C2 carbon atom.

7. Composition in accordance with claim 1, wherein the alkoxy groups of the alkyl polyalkoxy sulphate salts are exclusively propoxy groups.

8. The composition of claim 7 wherein the alkoxy groups are 3 to 13 propoxy groups on average.

9. The composition of claim 8, wherein the alkoxy groups are 4 to 10 propoxy groups on average.

10. Composition in accordance with claim 1, wherein the proportion of the salts of the alkyl polyalkoxy sulphates is greater than 80 to 95% by weight.

11. Composition in accordance with claim 1, wherein the concentration of water is 5 to 18% by weight.

12. Composition in accordance with claim 1, wherein the salts are selected from the group consisting of sodium salts, potassium salts, and mixtures thereof.

13. Composition in accordance with claim 1 having a pour point of less than −5° C.

14. The composition of claim 13 wherein the pour point is below −15° C.

15. Composition in accordance with claim 1 further comprising 0.05 to 5% by weight of a buffer.

16. The composition of claim 15 comprising 0.1 to 2% by weight buffers.

17. Composition in accordance with claim 1 containing 0 to 10% by weight of a non-ionic substance in accordance with DIN EN 13273:2001.

18. The composition of claim 17, wherein the non-ionic substances are present in an amount of up to 5% by weight.

19. Composition in accordance with claim 1 containing less than 8 weight % other ionic substances.

20. The composition of claim 19 wherein the other ionic substances are present in an amount of up to 4% by weight.

21. Composition in accordance with claim 1 comprising less than 5 weight % other compounds.

22. Method of producing the composition in accordance with claim 1 comprising at least the following steps:
    reacting in a falling film reactor an alkoxylated fatty alcohol with $SO_3$, wherein the alkoxylated fatty alcohol has in average 3 to 20 alkoxy groups, at least ⅔ of all alkoxy groups of the alkyl polyalkoxy sulphates are propoxy groups and the alkyl residue is a fatty alcohol residue with 13 to 18 carbon atoms or is a mixture of C12 and C13 fatty alcohol residues,
    performing a gas/liquid-phase separation and
    neutralizing the liquid phase with an alkali hydroxide in aqueous solution comprising more than 25 weight % alkali hydroxide.

23. Method in accordance with claim 22, whereby the reaction takes place with $SO_3$ at 20 to 60° C.

24. The method of claim 23, wherein the reaction takes place at 25 to 40° C.

25. Method in accordance with claim 22, whereby the neutralization takes place at 30 to 70° C., and with aqueous alkali hydroxides containing less than 55% by weight alkali hydroxide.

26. The method of claim 25 wherein the neutralization takes place at 50 to 60° C.

27. The method of claim 25, wherein the alkali hydroxides are selected from the group consisting of sodium hydroxide and potassium hydroxide, and mixtures thereof.

28. Method in accordance with claim 22, whereby on completion of the neutralization the pH of the neutralized liquid phase is greater than 10.

29. The method of claim 28, wherein the pH is 11 or greater.

30. Method in accordance with claim 22, wherein an $SO_3$/air mixture with 3 to 10% by weight $SO_3$ is used.

31. Method in accordance with claim 22, wherein the alkoxylated fatty alcohol has exclusively propoxy groups.

32. The method of claim 31, wherein the alkoxylated fatty alcohol has 3 to 13 propoxy groups on average.

33. The method of claim 32, wherein the alkoxylated fatty alcohol has 4 to 10 propoxy groups on average.

34. Method of facilitating crude oil extraction from a downhole formation, comprising:
    diluting the composition of claim 1 with water to a desired concentration;
    injecting the composition into the formation to form a microemulsion and facilitate recovery.

35. The method of claim 34, wherein the composition is injected into the formation for tertiary oil recovery.

36. Highly-concentrated alkyl polyalkoxy sulphate composition, comprising:
    a) more than 80% by weight salts of alkyl polyalkoxy sulphates, whereby the alkyl polyalkoxy sulphates have in average 3 to 20 alkoxy groups, at least ⅔ of all alkoxy groups of the alkyl polyalkoxy sulphates are propoxy groups and the alkyl residue is a fatty alcohol residue with 14 to 18 carbon atoms and
    b) 5 to below 20% by weight water;
    said compositions being flowable at least at 25° C., wherein flowable means having a viscosity of below 10000 mPas measured in accordance with DIN 53019 at 25° C. and with a shear rate of $D=10\ s^{-1}$.

37. Highly-concentrated alkyl polyalkoxy sulphate composition, comprising:
    a) more than 80% by weight salts of alkyl polyalkoxy sulphates, whereby the alkyl polyalkoxy sulphates have in average 3 to 20 alkoxy groups, at least ⅔ of all alkoxy groups of the alkyl polyalkoxy sulphates are propoxy groups and the alkyl residue is a linear fatty alcohol residue with 12 to 18 carbon atoms or a mixture of linear and branched fatty alcohol residues with 12 to 18 carbon atoms and
    b) 5 to below 20% by weight water;
said compositions being flowable at least at 25° C., wherein flowable means having a viscosity of below 10000 mPas measured in accordance with DIN 53019 at 25° C. and with a shear rate of $D=10\ s^{-1}$.

38. The composition of claim 37, wherein the alkyl residue is a linear fatty alcohol residue with 12 to 18 carbon atoms.

* * * * *